(12) United States Patent
Yin et al.

(10) Patent No.: US 9,210,936 B2
(45) Date of Patent: *Dec. 15, 2015

(54) BIOCIDAL COMPOSITIONS AND METHODS OF USE

(75) Inventors: Bei Yin, Buffalo Grove, IL (US); Sheila M. Tinetti, Vernon Hills, IL (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/345,230

(22) PCT Filed: Sep. 7, 2012

(86) PCT No.: PCT/US2012/054060
§ 371 (c)(1),
(2), (4) Date: Mar. 14, 2014

(87) PCT Pub. No.: WO2013/039769
PCT Pub. Date: Mar. 21, 2013

(65) Prior Publication Data
US 2014/0349975 A1    Nov. 27, 2014

Related U.S. Application Data

(60) Provisional application No. 61/534,975, filed on Sep. 15, 2011.

(51) Int. Cl.
| | | |
|---|---|---|
| *A01N 57/34* | (2006.01) | |
| *A01N 33/08* | (2006.01) | |
| *A01N 57/20* | (2006.01) | |
| *C02F 1/50* | (2006.01) | |
| *C02F 103/10* | (2006.01) | |

(52) U.S. Cl.
CPC ............... *A01N 57/34* (2013.01); *A01N 33/08* (2013.01); *A01N 57/20* (2013.01); *C02F 1/50* (2013.01); *C02F 2103/10* (2013.01); *C02F 2303/04* (2013.01); *C02F 2305/02* (2013.01)

(58) Field of Classification Search
None
See application file for complete search history.

(56) References Cited

U.S. PATENT DOCUMENTS

| | | | |
|---|---|---|---|
| 4,916,123 A | 4/1990 | Donofrio et al. | |
| H1265 H * | 12/1993 | Brady et al. | 514/665 |
| 5,741,757 A * | 4/1998 | Cooper et al. | 504/153 |
| 6,784,168 B1 | 8/2004 | Jones et al. | |
| 2003/0228373 A1 | 12/2003 | Ludensky et al. | |
| 2005/0040116 A1 * | 2/2005 | Purdy et al. | 210/749 |
| 2012/0178722 A1 | 7/2012 | Yin | |
| 2012/0196836 A1 | 8/2012 | Yin | |

FOREIGN PATENT DOCUMENTS

| | | | |
|---|---|---|---|
| CA | 2000282 | * | 10/1990 |
| WO | 0004777 | A1 | 2/2000 |
| WO | 2005074688 | A2 | 8/2005 |
| WO | 2009015088 | A2 | 1/2009 |
| WO | 2009015089 | A2 | 1/2009 |
| WO | 2011016909 | A1 | 2/2011 |
| WO | 2012019360 | A1 | 2/2012 |

* cited by examiner

*Primary Examiner* — Jennifer A Berrios
(74) *Attorney, Agent, or Firm* — Tifani M. Edwards

(57) ABSTRACT

Provided are biocidal compositions comprising: a hydroxymethyl-substituted phosphorus compound and 2-(decylthio) ethanamine compound. The compositions are useful for controlling microorganisms in aqueous or water-containing systems.

8 Claims, No Drawings

BIOCIDAL COMPOSITIONS AND METHODS OF USE

BACKGROUND

The invention relates generally to biocidal compositions and methods of their use for the control of microorganisms in aqueous and water-containing systems. The compositions comprise a hydroxymethyl-substituted phosphorus compound and 2-(decylthio)ethanamine.

Protecting water-containing systems from microbial contamination is critical to the success of many industrial processes, including oil or natural gas production operations. In oil and gas operations, microorganism contamination from both aerobic and anaerobic bacteria can cause serious problems such as reservoir souring (mainly caused by anaerobic sulfate-reducing bacteria (SRB)), microbiologically influenced corrosion (MIC) on metal surfaces of equipment and pipelines, and degradation of polymer additives.

Biofilm, formed by microorganism growth, can create even greater problems and potentially causes huge economic losses in industry through equipment and pipeline corrosion, system plugging, product failing, and energy losses. Biofilm is formed by a buildup of layers of microorganisms occupying a structured community encapsulated within a self developed polymeric matrix. Microorganisms within the biofilm are known as sessile microorganisms, whereas free floating non-biofilm microorganisms are planktonic.

By growing in biofilms, sessile microorganisms are more tolerant to antimicrobial treatment and biocides that are effective against planktonic microorganisms may not exhibit equivalent efficacy against sessile bacteria inside a biofilm. Moreover, even biocides that are effective against biofilm-associated microorganisms are not necessarily efficient at removing a biofilm from a contaminated surface. The physical presence of the remnants of the biofilm (e.g., exopolysaccharides and dead bacteria cells) still plug systems and oil/gas reservoirs, and lead to an uneven availability of oxygen to e.g., a metal surface that allows corrosion to occur. Thus, killing microorganisms in a biofilm without removing the biofilm from a surface may not always solve the contamination problem.

The problem addressed by this invention is the provision of biocides that are effective against a wide range of microorganisms, that may be used in reduced amounts so as to be economically and environmentally attractive, and/or that exhibit the ability to remove biofilm.

STATEMENT OF INVENTION

In one aspect, the invention provides biocidal compositions. The compositions are useful for controlling microbial growth in aqueous or water-containing systems, including for applications in the oil and natural gas industry. The compositions of the invention comprise: a hydroxymethyl-substituted phosphorus compound selected from the group consisting of a tetrakis(hydroxymethyl)phosphonium salt, a $C_1$-$C_3$ alkyl- or $C_2$-$C_3$ alkenyl-tris(hydroxymethyl)phosphonium salt, and tris(hydroxymethyl)phosphine; and 2-(decylthio)ethanamine.

In a second aspect, the invention provides a method for controlling microorganisms in aqueous or water-containing systems. The method comprises treating the system with an effective amount of a biocidal composition as described herein.

DETAILED DESCRIPTION

As noted above, the invention provides biocidal compositions and methods of using them in the control of microorganisms. The compositions comprise a hydroxymethyl-substituted phosphorus compound and 2-(decylthio)ethanamine. It has surprisingly been discovered that combinations of a hydroxymethyl-substituted phosphorus compound and 2-(decylthio)ethanamine as described herein, at certain weight ratios, are synergistic when used for microorganism control in aqueous or water-containing media. That is, the combined materials result in improved biocidal properties than would otherwise be expected based on their individual performance at the particular use-concentration. The observed synergy permits reduced amounts of the materials to be used to achieve acceptable biocidal properties.

In addition to exhibiting synergy, the compositions of the invention are effective at controlling both aerobic and anaerobic microorganisms. Further, the compositions exhibit the ability to remove biofilm. As a result of these attributes, the compositions are well suited for use in various applications, including in the oil and natural gas industry where biocidal agents are needed that are capable of controlling microorganisms, including aerobic and anaerobic microorganisms, and that are effective against biofilm.

For the purposes of this specification, the meaning of "microorganism" includes, but is not limited to, bacteria, fungi, algae, and viruses. The words "control" and "controlling" should be broadly construed to include within their meaning, and without being limited thereto, inhibiting the growth or propagation of microorganisms, killing microorganisms, disinfection, and/or preservation against microorganism growth.

The composition of the invention comprises: a hydroxymethyl-substituted phosphorus compound and 2-(decylthio)ethanamine (DTEA).

The hydroxymethyl-substituted phosphorus compound for use in the invention is selected from the group consisting of a tetrakis(hydroxymethyl)phosphonium salt, a $C_1$-$C_3$ alkyl- or $C_2$-$C_3$ alkenyl-tris(hydroxymethyl)phosphonium salt, and tris(hydroxymethyl)phosphine. Such compounds are generally available both in undissolved form or as aqueous solutions. In one embodiment of the invention, the hydroxymethyl-substituted phosphorus compound is a tetrakis(hydroxymethyl)phosphonium salt, such as the chloride, phosphate, or sulfate salt. A preferred compound is tetrakis(hydroxymethyl)phosphonium sulfate (THPS). THPS is available from The Dow Chemical Company as AQUCAR™ THPS 75, a 75 wt % solution in water. Of course, more than one of the recited hydroxymethyl-substituted phosphorus compounds can be combined for use in the present invention; in such cases, ratios and concentrations are calculated using the total weight of all hydroxymethyl-substituted phosphorus compounds.

The 2-(decylthio)ethanamine of the invention may be the free base or it may be in the form of an acid salt. The suitable acid can be a wide variety of acids which form acid salts with 2-(decylthio)ethanamine. Examples of suitable acids include HCl, $HNO_3$, HBr, $H_3PO_4$, $H_2SO_4$ or other mineral acids; or weaker acids such as acetic, propionic, butyric, glycolic, or other monofunctional or polyfunctional carboxylic acids. A preferred acid is HCl. 2-(Decylthio)ethanamine is commercially available or it may be readily prepared by those skilled in the art.

In some embodiments, the weight ratio of the hydroxymethyl-substituted phosphorus compound to 2-(decylthio)ethanamine in the compositions of the invention is between 50:1 and 1:50, alternatively between 20:1 and 1:20, alternatively between 10:1 and 1:10, alternatively between 8:1 and 1:4, or alternatively between 7.6:1 and 1:3.4.

The compositions of the invention may contain additional components including, but not limited to, surfactants, stabilizers, demulsifier, polymers, and/or additional biocides.

The compositions of the invention are useful for controlling microorganisms in aqueous or water-containing systems. In some embodiments, the aqueous or water containing system comprises at least 40 weight percent, alternatively at least 60 weight percent, or alternatively at least 80 weight percent of water. Non-limiting examples of aqueous or water containing systems with which the inventive compositions may be used to control microorganisms include those present in oil and natural gas applications. Examples of such systems include, but are not limited to, injection and produced water, source water for waterflooding and hydraulic fracturing such as pond water and holding tank water, functional fluids such as drilling muds, completion or workover fluids, hydrotest fluids, stimulation fluids, packer fluids, and fracturing fluids, oil and gas wells, separation, storage, and transportation systems, oil and gas pipelines, oil and gas vessels, or fuel.

The inventive compositions may also be used for controlling microorganisms in other industrial aqueous and water containing/contaminated systems, such as cooling water, air washer, heat exchangers, boiler water, pulp and paper mill water, other industrial process water, ballast water, wastewater, metalworking fluids, latex, paint, coatings, adhesives, inks, tape joint compounds, pigment, water-based slurries, swimming pool, personal care and household products such as detergent, membrane and filtration systems, toilet bowl, textiles, leather and leather production system, or a system used therewith.

In some embodiments, the microorganism being controlled with the compositions of the invention is anaerobic, such as sulfate-reducing bacteria (SRB). In some embodiments, the microorganism being controlled is anaerobic, such as SRB, and the aqueous system contains a reducing agent, such as sulfide.

A person of ordinary skill in the art can readily determine, without undue experimentation, the concentration of the composition that should be used in any particular application. By way of illustration, a suitable actives concentration (total for both the hydroxymethyl-substituted phosphorus compound and 2-(decylthio)ethanamine) is typically between 1 and 2500 ppm, alternatively between 5 and 1000 ppm, alternatively between 10 and 500 ppm, or alternatively between 50 and 300 ppm, based on the total weight of the aqueous or water-containing system including the biocides. In some embodiments for oil and gas applications, it is preferred that active concentrations of the composition range from about 10 to about 300 ppm by weight, preferably about 30 to 100 ppm, for top side treatment, and from about 30 to about 500 ppm, preferably about 50 to about 250 ppm, for downhole treatment.

The components of the inventive compositions can be added to the aqueous or water-containing system separately, or preblended prior to addition. A person of ordinary skill in the art can easily determine the appropriate method of addition. The composition can be used in the system with other additives such as, but not limited to, surfactants, ionic/nonionic polymers and scale and corrosion inhibitors, oxygen scavengers, and/or additional biocides.

Unless otherwise indicated, numeric ranges, for instance as in "from 2 to 10," are inclusive of the numbers defining the range (e.g., 2 and 10).

Unless otherwise indicated, ratios, parts, and the like are by weight.

The following examples are illustrative of the invention but are not intended to limit its scope. Unless otherwise indicated, ratios, percentages, parts, and the like used herein are by weight.

EXAMPLES

The synergy indexes reported in the following examples are calculated using the following equation:

Synergy Index=$Ca/CA+Cb/CB$

Ca: Concentration of biocide A required to achieve a certain level of bacterial kill when used in combination with B CA: Concentration of biocide A required to achieve a certain level of bacterial kill when used alone Cb: Concentration of biocide B required to achieve a certain level of bacterial kill when used in combination with A CB: Concentration of biocide B required to achieve a certain level of bacterial kill when used alone.

A synergy index (SI) of 1 indicates additivity, a synergy index of less than 1 indicates synergy, and a synergy index greater than 1 indicates antagonism.

Example 1

Synergistic Effect of Tetrakis(Hydroxymethyl)Phosphonium Sulfate (THPS) and 2-(Decylthio)Ethanamine (DTEA), against Anaerobic Bacteria Inside an anaerobic chamber (Bactron anaerobic chamber), a deoxygenated sterile salt solution (3.1183 g of NaCl, 1.3082 mg of $NaHCO_3$, 47.70 mg of KCl, 72.00 mg of $CaCl_2$, 54.49 mg of $MgSO_4$, 172.28 mg of $Na2SO_4$, 43.92 mg of $Na_2CO_3$ in 1 L water) is inoculated with *Desulfovibrio longus* ATCC 51456 to a final bacterial concentration of $10^6$ to $10^7$ CFU/mL. Aliquots of this cell suspension are then treated with THPS, DTEA, and THPS/DTEA blends, at selected active concentrations. After the treated cell suspensions are incubated at 35° C. for 2 hours, the biocidal efficacy is determined by minimum tested biocide concentration for complete bacterial kill in the aliquots (MBC). Table 1 summarizes the efficacy of each biocide and their blends, and the Synergy Index of each combination.

TABLE 1

Biocidal efficacy of THPS, DTEA, THPS/DTEA combinations, and Synergy Index

| Active weight ratio of | Concentration (ppm active) for anaerobic bacteria kill | | |
|---|---|---|---|
| THPS:DTEA | THPS | DTEA | Synergy Index |
| 1:0 | 19.75 | 0.00 | |
| 11.4:1 | 19.75 | 1.76 | 1.09 |
| 7.6:1 | 13.18 | 1.76 | 0.75 |
| 3.4:1 | 8.77 | 2.63 | 0.57 |
| 1:1 | 5.87 | 5.93 | 0.59 |
| 1:3.4 | 3.06 | 10.37 | 0.67 |
| 0:1 | 0.00 | 20.00 | |

As shown in Table 1, THPS in combination with DTEA exhibits a synergistic effect against anaerobic bacteria.

Example 2

Sessile Bacteria Kill with THPS/DTEA Combinations

Biofilms of *Desulfovibrio longus* ATCC 51456 are grown in Calgary Biofilm Device (Innovotech, Alberta, Canada) at 35° C. and under anaerobic conditions for 72 hours with shaking (125 rpm). Modified Baar's Medium (ATCC #1249 Broth) is used as culture medium and the medium is changed after 48 hrs of incubation. After the incubation period, pegs are rinsed with deoxygenated 0.85% NaCl solution and then treated with THPS and THPS/DTEA blend (5:1 and 3:1 active weight ratio) in a deoxygenated salt solution (3.1183 g of NaCl, 1.3082 mg of NaHCO3, 47.70 mg of KCl, 72.00 mg of CaCl2, 54.49 mg of MgSO4, 172.28 mg of Na2SO4, 43.92 mg of Na2CO3, 20 mg of Fe(NH4) 2 (SO4) 2.6H2O in 1 L water) for 2 hours. After biocide treatment, the pegs are rinsed again with deoxygenated sterile 0.85% NaCl solution and sessile cells attached on the pegs are released from the peg surface by sonication (SPER Scientific) for 16 minutes. The viable bacteria are then enumerated using a serial dilution method. The biocidal efficacy of tested biocides for 3 log 10 reduction of sessile bacteria is compared in Table 2.

TABLE 2

Biocidal efficacy against sessile bacteria

| Biocide | Concentration (ppm active) for 3 log$_{10}$ bacterial reduction |
|---|---|
| THPS | 50 |
| THPS:DTEA at 5:1 active weight ratio | 25 |
| THPS:DTEA at 3:1 active weight ratio | 25 |

Example 3

Biofilm Removal with THPS/DTEA Combinations

Grow and treat biofilms of *Desulfovibrio longus* ATCC 51456 with biocides, using the same method described in example 2. After biocide treatment, the pegs are rinsed with deoxygenated sterile 0.85% NaCl solution and then the total biofilm left on each peg is measured as following description. The biofilm is fixed with 99% methanol and, after air drying, the pegs are stained with 2% (w/v) crystal violet and washed with tap water. The pegs are then air dried and the crystal violet bound to the biofilm is extracted with 33% glacial acetic acid. The total remaining biofilm is determined by the optical density (OD) of the extracted solution at 580 nm. Table 3 compares the remaining biofilm after biocide treatment for the tested biocides.

TABLE 3

Remaining biofilm (optical density of biofilm captured crystal violet) after biocide treatment

| Biocide | Concentration (ppm active) | OD$_{580}$ |
|---|---|---|
| THPS | 100 | 0.68 |
|  | 50 | 0.57 |
| THPS:DTEA at 5:1 active weight ratio | 100 | 0.59 |
|  | 50 | 0.47 |
| THPS:DTEA at 3:1 active weight ratio | 100 | 0.42 |
|  | 50 | 0.41 |

Table 3 shows that THPS/DTEA blend has improved biofilm removal efficacy compared to THPS alone.

What is claimed is:

1. A synergistic composition comprising tetrakis(hydroxymethyl)phosphonium sulfate and 2-(decylthio)ethanamine, wherein the weight ratio of tetrakis(hydroxymethyl) phosphonium sulfate to 2-(decylthio)ethanamine is between 8:1 and 1:4.

2. The composition of claim 1 wherein the 2-(decylthio) ethanamine is a hydrochloric acid salt.

3. A method for controlling microorganisms in an aqueous or water-containing system, the method comprising treating the system with the composition of claim 1.

4. The method of claim 3 wherein the aqueous or water-containing system is used or is present in oil or gas production.

5. The method of claim 4 wherein the oil or gas production comprises injection and produced water, source water for waterflooding and hydraulic fracturing, pond water, holding tank water, functional fluids, drilling muds, completion and workover fluids, hydrotest fluids, stimulation fluids, packer fluids, fracturing fluids, oil and gas wells, separation, storage and transportation systems, oil and gas pipelines, oil and gas vessels, or fuel.

6. The method of claim 3 wherein the aqueous or water-containing system is cooling water, air washer, heat exchangers, boiler water, pulp and paper mill water, other industrial process water, ballast water, wastewater, metalworking fluids, latex, paint, coatings, adhesives, inks, tape joint compounds, pigment, water-based slurries, swimming pool, personal care and household products, detergent, membrane and filtration systems, toilet bowel, textiles, leather and leather production system, or a system used therewith.

7. The method of claim 3 wherein the microorganisms are anaerobic bacteria.

8. The method of claim 3 wherein the microorganisms are aerobic bacteria.

* * * * *